(12) United States Patent
Yu et al.

(10) Patent No.: US 8,804,115 B2
(45) Date of Patent: Aug. 12, 2014

(54) SYSTEMS AND METHODS FOR PERFORMING OPTICAL SPECTROSCOPY USING A SELF-CALIBRATING FIBER OPTIC PROBE

(75) Inventors: Bing Yu, Cary, NC (US); Nirmala Ramanujam, Chapel Hill, NC (US)

(73) Assignee: Duke University, Durham, NC (US)

( * ) Notice: Subject to any disclaimer, the term of this patent is extended or adjusted under 35 U.S.C. 154(b) by 891 days.

(21) Appl. No.: 12/989,591

(22) PCT Filed: Apr. 27, 2009

(86) PCT No.: PCT/US2009/041857
§ 371 (c)(1),
(2), (4) Date: Aug. 8, 2011

(87) PCT Pub. No.: WO2009/132360
PCT Pub. Date: Oct. 29, 2009

(65) Prior Publication Data
US 2011/0295541 A1    Dec. 1, 2011

Related U.S. Application Data

(60) Provisional application No. 61/047,818, filed on Apr. 25, 2008.

(51) Int. Cl.
*G01J 3/00* (2006.01)
*G01J 3/40* (2006.01)
*G01J 3/42* (2006.01)
*G01J 3/28* (2006.01)
*G01N 21/47* (2006.01)
*G01J 3/02* (2006.01)
*G01N 21/27* (2006.01)
*G01N 21/49* (2006.01)

(52) U.S. Cl.
CPC .... *G01J 3/02* (2013.01); *G01J 3/28* (2013.01); *G01N 21/474* (2013.01); *G01J 3/0218* (2013.01); *G01N 21/274* (2013.01); *G01J 2003/2866* (2013.01); *G01N 2201/082* (2013.01); *G01N 21/49* (2013.01)
USPC ............................ 356/300; 356/302; 356/319

(58) Field of Classification Search
CPC ...................................................... G01J 3/0218
USPC .......................... 356/330–334, 400–425, 456
See application file for complete search history.

(56) References Cited

U.S. PATENT DOCUMENTS 5,125,747 A    6/1992    Sayegh et al.
(Continued)

FOREIGN PATENT DOCUMENTS

WO    WO 02/26152 A1    4/2002
WO    WO 2006/059226 A1    6/2006

OTHER PUBLICATIONS

Extended European Search Report for European Patent Application No. 09734638.1 (Jul. 3, 2013).
(Continued)

*Primary Examiner* — Gregory J Toatley
*Assistant Examiner* — Maurice Smith
(74) *Attorney, Agent, or Firm* — Jenkins, Wilson, Taylor & Hunt, P.A.

(57) ABSTRACT

Systems and methods for performing optical spectroscopy using a self-calibrating fiber optic probe are disclosed. One self-calibrating fiber optic probe includes a sensing channel for transmitting illumination light to a specimen and for collecting spectral data of the specimen. The spectral data includes the illumination light diffusely reflected from the specimen at one or more wavelengths. The self-calibrating fiber optic probe may also include a calibration channel for transmitting calibration light. The calibration light and the illumination light are generated simultaneously from a common light source. The calibration channel collects calibration spectral data associated with the calibration light contemporaneously with the collection of the spectral data of the specimen.

43 Claims, 4 Drawing Sheets

(56) References Cited

U.S. PATENT DOCUMENTS

| | | | |
|---|---|---|---|
| 5,452,723 | A | 9/1995 | Wu et al. |
| 5,792,049 | A | 8/1998 | Eppstein et al. |
| 5,860,421 | A | 1/1999 | Eppstein et al. |
| 5,953,477 | A | 9/1999 | Wach et al. |
| 6,045,502 | A | 4/2000 | Eppstein et al. |
| 6,052,177 | A | 4/2000 | Millar et al. |
| 6,055,451 | A | 4/2000 | Bambot et al. |
| 6,226,541 | B1 | 5/2001 | Eppstein et al. |
| 6,351,306 | B1 | 2/2002 | Tedesco et al. |
| 6,377,840 | B1 | 4/2002 | Gritsenko et al. |
| 6,564,088 | B1 | 5/2003 | Soller et al. |
| 6,678,541 | B1 | 1/2004 | Durkin et al. |
| 6,870,620 | B2 | 3/2005 | Faupel et al. |
| 7,239,385 | B2 * | 7/2007 | Schmitz et al. ............ 356/319 |
| 7,333,189 | B2 | 2/2008 | Fulghum et al. |
| 7,570,988 | B2 | 8/2009 | Ramanujam et al. |
| 7,835,786 | B2 | 11/2010 | Palmer et al. |
| 2004/0015062 | A1 | 1/2004 | Ntziachristos et al. |
| 2004/0224315 | A1 | 11/2004 | Villa et al. |
| 2005/0162646 | A1 | 7/2005 | Tedesco et al. |

OTHER PUBLICATIONS

International Search Report for International Application No. PCT/US2009/041857 (Dec. 23, 2009).

(Quan) Liu et al., "Experimental Proof of the Feasibility of Using an Angled Fiber-optic Probe for Depth-sensitive Flurorescence Spectroscopy of Turbid Media," Optics Letters, vol. 29, No. 17, pp. 2034-2036 (Sep. 1, 2004).

Diamond et al., "Measurement of Fluorophore Concentrations and Fluorescence Quantum Yield in Tissue-Simulating Phantoms Using Three Diffusion Models of Steady-State Spatially Resolved Fluorescence," Physics in Medicine and Biology, vol. 48, pp. 4135-4149 (2003).

Diamond et al., "Quantification of Fluorophore Concentration in Tissue-Simulating Media by Fluorescence Measurements with a Single Optical Fiber," Applied Optics, vol. 42, No. 13, pp. 2436-2444 (May 1, 2003).

Lubawy et al., "Endoscopically compatible near infrared photon migration probe," Optics Letters, 29(17), 2022-2024 (2004).

Manos et al., "Optical Fiber Design Using Evolutionary Strategies," Engineering Computations, vol. 21, No. 6, pp. 564-576 (2004).

McClain et al., "Optical Absorption and Fluorescence Spectral Imaging Using Fiber Bundle Image Compression," Applied Spectroscopy, 53(9): 1118-1122 (1999).

Nichols et al., "Design and testing of a white-light steady-state diffuse reflectance spectrometer for determination of optical properties of highly scattering systems," Appl. Opt., 36(1), pp. 93-104 (1997).

Pfefer et al., "Influence of Illumination-Collection Geometry on Fluorescence Spectroscopy in Multilayer Tissue," Medical and Biological Engineering and Computing, vol. 42, No. 5, pp. 669-673 (Sep. 2004).

Pogue et al., "Fiber-Optic Bundle Design for Quantitative Fluorescence Measurement From Tissue," Applied Optics, vol. 37, Issue 31, p. 7429-7436 (Nov. 1, 1998).

Skala et al., "An Investigation of Probe Geometry Designs for the Optical Spectroscopic Diagnosis of Epithelial Pre-Cancers and Cancers," Lasers Surg Med, 34(1), 25-38 (2004).

Thueler et al;., "In Vivo Endoscopic Tissue Diagnostics Based on Spectroscopic Absorption, Scattering, and Phase Function Properties," Journal of Biomedical Optics, vol. 8, No. 3, pp. 495-503 (Jul. 2003).

Utzinger et al., "Fiber optic probes for biomedical optical spectroscopy," J Biomed Opt, 8(1):pp. 121-147 (2003).

Zhu et al., "Effect of Fiber Optic Probe Geometry on Depth-resolved Fluorescence Measurements From Epithelial Tissues: A Monte Carlo Simulation," Journal of Biomedical Optics, vol. 8, No. 2, p. 237-247 (Apr. 2003).

Zhu et al., "Use of a Multiseparation Fiber Optic Probe for the Optical Diagnosis of Breast Cancer," Journal of Biomedical Optics, vol. 10, No. 2, pp. 024032-1-024032-13 (Mar./Apr. 2005).

* cited by examiner

SYSTEMS AND METHODS FOR PERFORMING OPTICAL SPECTROSCOPY USING A SELF-CALIBRATING FIBER OPTIC PROBE

RELATED APPLICATIONS

This application claims the benefit of U.S. Provisional Patent Application Ser. No. 61/047,818, filed Apr. 25, 2008, the disclosure of which is incorporated herein by reference in its entirety.

GOVERNMENT INTEREST

This presently disclosed subject matter was made with U.S. Government support under Grant No. 1R01CA100559 awarded by NIH. Thus, the U.S. Government has certain rights in the presently disclosed subject matter.

TECHNICAL FIELD

The subject matter disclosed herein relates to optical spectroscopy and calibration techniques pertaining to fiber optic measurement instruments. More particularly, the subject matter disclosed herein relates to systems and methods for performing optical spectroscopy using a self-calibrating fiber optic probe.

BACKGROUND

Diffuse reflectance spectroscopy (DRS) is sensitive to the absorption and scattering properties of biological molecules in tissue and therefore can be used as a noninvasive in vivo tool to obtain quantitative information about the physiological and morphological properties (e.g., biomarkers) of human tissue. Thus, DRS can be utilized specifically as a diagnostic tool to detect various diseases that alter human tissue properties. Potential clinical applications of DRS include precancer detection and cancer diagnostics, intraoperative tumor margin assessment, and monitoring of tumor response to chemotherapy. Fiber optic probes are commonly used to deliver illumination light to, and collect diffusely reflected light from, a tissue specimen for DRS measurements. However, in order for DRS to be utilized in a clinic, frequent calibration is typically required to correct or compensate for a number of factors, such as lamp intensity fluctuations, wavelength-dependent instrument response, interdevice variations, and fiber bending losses that occur while a measurement is taken.

Calibration techniques presently used by biophotonics researchers typically rely on measurements using power meters, reflectance standards, and/or tissue phantoms (i.e., models that simulate human tissue and blood vessels). These calibration procedures are usually performed after the clinical measurements are completed. One particular DRS calibration method involves a two-step calibration procedure that utilizes the measured spectra of a spectrally flat diffuse reflectance standard (i.e., a reflective Spectralon puck) and a phantom of known optical properties in order to obtain the absolute reflectance spectra of a tissue sample. For example, a calibrated reference phantom spectrum is obtained by dividing the collected phantom spectrum with the collected puck spectrum. Similarly, a calibrated tissue spectrum is obtained by dividing a collected tissue spectrum with a second collected puck spectrum (i.e., a 2nd spectrum measurement of the same calibration puck). More specifically, calibration is performed by dividing the tissue spectra point by point by the spectra of the puck. Afterwards, a ratio of the calibrated tissue spectrum and the calibrated reference phantom spectrum is input into an inverse Monte Carlo model, which in turn extracts the optical properties of the tissue.

The aforementioned calibration of the tissue spectrum against a reference phantom is needed to put the experimental and Monte Carlo simulated data on the same scale. This is typically necessary no matter what type of calibration method is employed. However, the calibration of the tissue spectra and reference phantom spectra to the puck spectra is carried out to account for day-to-day system variations that occur between the time of the tissue measurement and the time of the reference phantom measurement.

There are a number of limitations associated with spectral data calibration methods currently utilized. Notably, these calibration methods fail to correct or compensate for real-time system fluctuations, such as variations in lamp intensity. For example, a given DRS illumination source typically requires at least 30 minutes of warm-up time to prevent significant light intensity fluctuations. However, the 30 minute warm-up period can pose considerable unwanted delays in a clinical setting, such as an operating room. Remarkably, light intensity of a light source can change as much as 25% during the warm-up period and even 3% afterwards. These variations in intensity are significant considering a 5% change in light intensity can introduce approximately 20% error in the extraction of optical properties from a tissue sample.

Another problem that arises in optical spectroscopy is the error caused by bending the optical fibers of the probe. Sharp bending frequently occurs in clinical applications, such as endoscopy, where the fiber optic probe is manually handled. For example, bending the detection arm (all 200 µm fibers) of the probe to a diameter of 3 cm (three turns) causes 6% light intensity attenuation, while bending the probe even further to a diameter of 2 cm can cause 11% attenuation in light intensity. As mentioned above, a 5% change in intensity can result in approximately 20% error in extracted optical properties from a tissue specimen.

Traditional calibration techniques typically rely on measurements from tissue phantoms and/or a diffuse reflectance standard that are usually performed after the clinical measurements are completed. Although these traditional calibration methods are successful in correcting instrument throughputs and remove day-to-day system drifts, none of the calibration methods are able to correct for real-time lamp fluctuations and fiber-bending loss while the specimen measurement is made. Similarly, all traditional calibration methods require at least 30 minutes for warming up the light source and a time-consuming calibration test procedure that is separate from the collection of the tissue sample spectra. As indicated previously, the reduction of unnecessary delays or procedures is extremely desirable in a clinical setting.

Thus, there remains a need for an improved system and method for performing optical spectroscopy using a self-calibrating fiber optical probe.

SUMMARY

The subject matter described herein includes systems and methods for performing optical spectroscopy using a self-calibrating fiber optical probe. According to one aspect, the self-calibrating fiber optic probe includes a sensing channel for transmitting illumination light to a specimen and for collecting spectral data of the specimen, wherein the spectral data includes the illumination light diffusely reflected from the specimen at one or more wavelengths. The self-calibrating fiber optic probe may also include a calibration channel for transmitting calibration light, wherein the calibration light and the illumination light are generated simultaneously from a common light source, and collecting calibration spectral data associated with the calibration light contemporaneously with the collection of the spectral data of the specimen.

BRIEF DESCRIPTION OF THE DRAWINGS

Preferred embodiments of the subject matter described herein will now be described with reference to the accompanying drawings, of which.

DETAILED DESCRIPTION

The subject matter described herein includes systems and methods for performing optical spectroscopy using a self-calibrating fiber optic probe. The present subject matter includes a fast, robust, and systematic calibration approach that can be used for correcting spectral data of a specimen obtained in real-time and with different instruments and probes. More specifically, the present subject matter includes a fiber optic probe with self-calibration capability configured for performing diffuse reflectance spectroscopy (DRS). The probe includes a built-in calibration channel that can be used to record the light source spectrum and instrument-fiber responses contemporaneously with tissue spectra measurements. Combined with a one-time single-reference phantom measurement, the self-calibrating fiber optic probe can provide instrument-independent optical properties.

Figure 1:
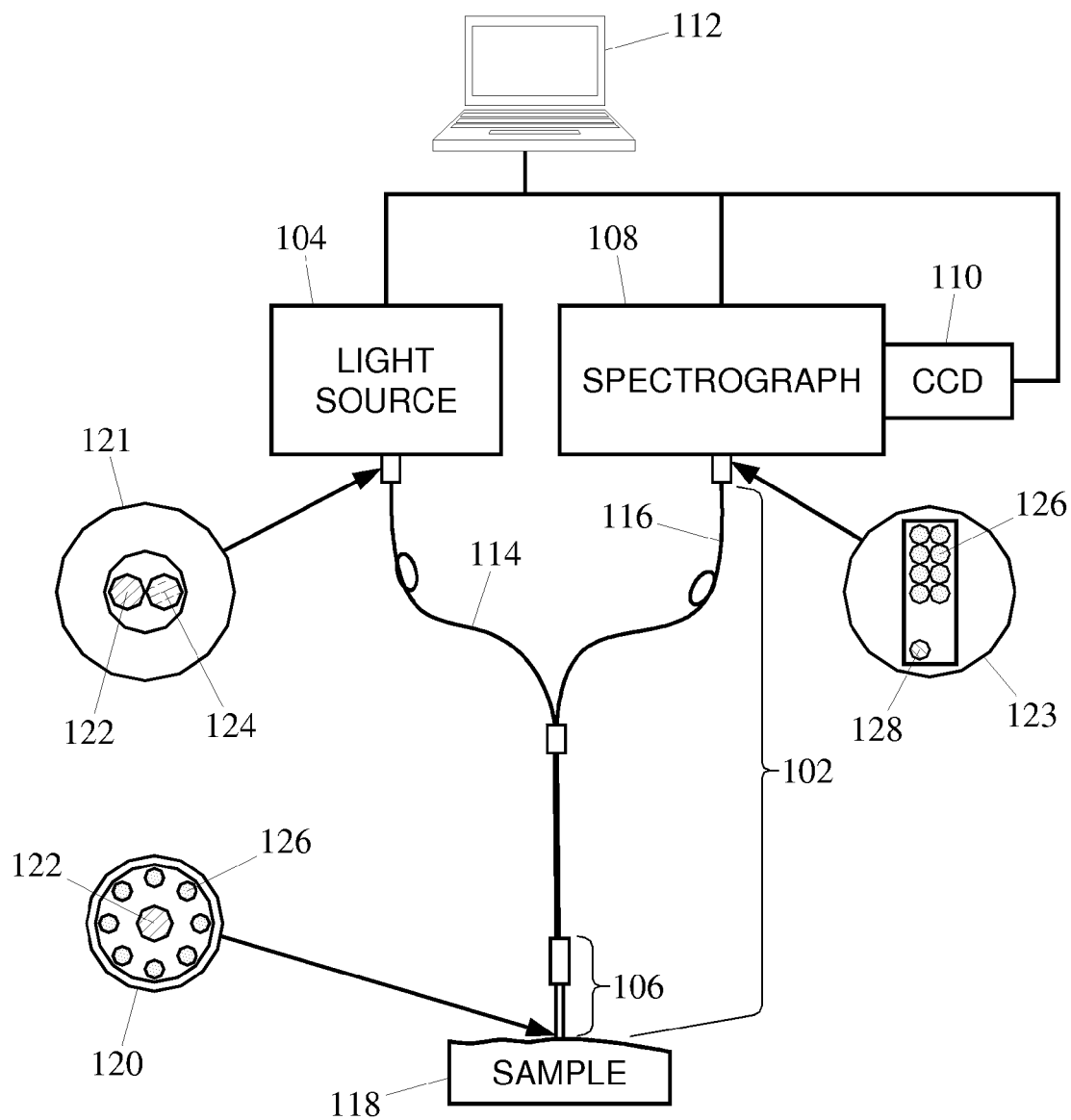
FIG. 1 is a block diagram of an optical spectrometer system that utilizes a self-calibrating fiber optical probe according to an embodiment of the subject matter described herein.

FIG. 1 depicts an exemplary optical DRS system 100 that includes a self-calibrating fiber optic probe 102. DRS system 100 may also include a light source 104, an imaging spectrograph 108, a charged-couple device (CCD) camera unit 110, and a processing unit 112 (e.g., a computer). In one embodiment, spectrograph 108 and CCD camera unit 110 are collectively known as a spectrometer. In one embodiment, fiber optic probe 102 comprises an illumination fiber "leg" 114 (which is coupled to light source 104), a collection fiber leg 116 (which is coupled to spectrograph 108), and a probe tip section 106, which may be used to interface with a specimen (e.g., sample 118), such a tissue mass or any turbid medium. In one embodiment, light source 104 may include a xenon lamp, a white light emitting diode (LED) source, or the like. In an alternate embodiment, a broadband light source with a monochromator (e.g., a scanning double-excitation monochromator) or simply a plurality of laser diodes may also be used in system 100 along with a plurality of photodetectors (e.g., photodiodes) used in lieu of spectrograph 108 and CCD 110. Also, self-calibrating fiber optic probe 102 may be adapted to accommodate any probe instrument. Possible probe adaptations include, but are not limited to, side firing probes and forward firing probes.

The illumination fiber leg 114 of probe 102 may include illumination source fiber 122, for illuminating the sample, and calibration source fiber 124, for internal calibration. In one embodiment, each of illumination source fiber 122 and calibration source fiber 124 are 600 µm diameter fibers. In another embodiment, a plurality of 200 µm diameter illumination source fibers (instead of a single 600 µm diameter illumination source fiber) and/or at least one 200 µm diameter calibration source fiber (instead of a single 600 µm diameter calibration source fiber) may be used for increased instrument flexibility. The collection fiber leg 116 may include eight detection fibers 126 that are coupled to spectrograph 108 and are configured to collect the diffusely reflected light from sample 118 at one or more wavelengths. In one embodiment, detection fibers 126 are 200 µm diameter fibers. Collection fiber leg 116 may also include at least one calibration return fiber 128 for collecting the calibration light (which, like the illumination light, is generated by light source 104) reflected by a reflective element 302 (see FIG. 3) and transmitting the reflected light to imaging spectrograph 108. In one embodiment, calibration return fiber 128 also comprises a 200 µm diameter fiber. Although cross-sectional view 123 shows one calibration return fiber 128, additional calibration return fibers may be used. For example, additional calibration return fibers may be implemented as backup return fibers (in case a primary return fiber fails) or if additional calibration channels are to be implemented in system 100. In one embodiment, all the fibers are made from the same materials (e.g., same fiber clad, core, etc.) and have the same numerical aperture (NA) for an identical bending response. In another embodiment, the at least one calibration source fiber 124 and the at least one illumination source fiber 122 are constructed from the same type of materials and include identical numerical apertures, core diameters and clad diameters and the at least one detection fiber and the at least one calibration return fiber are constructed from the same type of materials and include identical numerical apertures, core diameters and clad diameters (i.e., the source fibers may be different from the calibration return and detection fibers).

In one embodiment, the collected diffuse reflectance and beams of calibration light carried by the calibration return and detection fibers are diffracted and projected onto different areas of CCD camera 110 and recorded by processing unit 112. In one embodiment, a two-dimensional CCD camera 110 operates in a multi-track manner that enables it to obtain both the specimen spectrum and calibration spectrum (i.e., spectral data from light carried in calibration return fiber 124) simultaneously. There may be an equivalent of one, but not limited to one collection fiber spacing between the self-calibration and sensing areas on the CCD with no measurable cross talk. In one embodiment, a miniature spectrometer may be used for each channel (i.e., the sensing channel and calibration channel). Practically speaking, the at least one calibration return fiber may be coupled to a first spectrometer, while the at least one detection fiber may be coupled to a second spectrometer. Similarly, the at least one calibration return fiber and the at least one detection fiber may each instead be respectively coupled to a separate and dedicated spectrograph and/or photodetector.

Once the spectral data is received by the processing unit 112 from the spectrograph 108 and CCD camera 110, processing unit 112 may ultimately execute an algorithm to interpret the spectral data and extract the optical properties of sample 118 from the probe measurements. In one embodiment, the algorithm may include a Monte Carlo algorithm that is executed by processing unit 112. Similarly, the Monte Carlo algorithm may also include an inverse Monte Carlo reflectance algorithm or an inverse Monte Carlo fluorescence algorithm. An exemplary Monte Carlo algorithm suitable for use with the subject matter described herein is found in international patent application number PCT/US2007/006624 to Palmer and Ramanujam and U.S. patent application publication 2006/0247532 to Ramanujam et al. An exemplary scaling method for expediting calculations performed in the Monte Carlo algorithm is described in U.S. provisional patent application Ser. No. 60/903,177, filed Feb. 23, 2007. In an alternative embodiment, a diffusion algorithm or an inverse diffusion algorithm may be used instead of a Monte Carlo algorithm.

Figure 2:
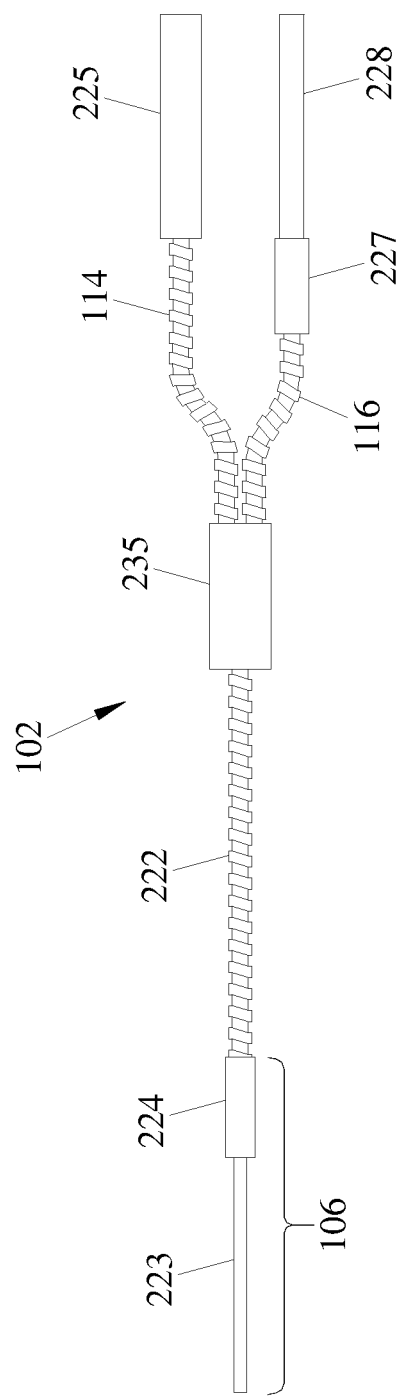
FIG. 2 is a diagram of an exemplary self-calibrating fiber optic probe according to an embodiment of the subject matter described herein.

FIG. 2 depicts a diagram of an exemplary self-calibrating fiber optic probe (e.g., probe 102) that may be interfaced with a specimen. In one embodiment, fiber optic probe 102 comprises a flexible steel sheathed tubing that contains a plurality of optical fibers. Although FIG. 2 depicts fiber optic probe 102 as having an "armored" jacket, any external covering may be used without departing from the scope of the present subject matter. Fiber optic probe includes a main portion 222 that terminates at probe tip portion 106 (which includes rigid probe tip 223 and calibration housing section 224) on one end and a breakout tube 235 on the opposite end. Breakout tube 235 allows for the bifurcation of main portion 222 into two different physical optical fiber groupings (e.g., illumination fiber leg 114 and collection fiber leg 116).

In addition to having two physical optical fiber groupings, fiber optic probe 102 may also comprise two separate "channels", each of which is distributed between both the illumination fiber leg 114 and collection fiber leg 116. Namely, a self-calibrating fiber optic probe may include a sensing channel and a built-in calibration channel. In one embodiment, the sensing channel includes at least one illumination source fiber (e.g., illumination source fiber 122) that traverses illumination fiber leg 114 and at least one detection fiber (e.g., detection fibers 126) that traverses collection fiber leg 116. Similarly, the calibration channel may comprise at least one calibration source fiber (e.g., calibration source fiber 124) that traverses illumination fiber leg 114 and at least one calibration return fiber (e.g., calibration return fibers 128) that traverses collection fiber leg 116. In one embodiment, the self-calibrating probe can be used to concurrently measure the spectral data of light source 104 and the spectral data of sample 118. Notably, this configuration is advantageous in a clinical setting because the configuration accounts for the real-time light source intensity fluctuations and fiber bending loss (i.e., light intensity fluctuations caused by bending the instrument). For example, the bending effect on illumination source fiber 122 is assumed to be the same as that of calibration source fiber 124. Also, light source warm-up time and separate calibration measurements are also unnecessary with a self-calibrating fiber optic probe. In addition, the sensing channel and the calibration channel may also refer to a first CCD channel on CCD camera 110 that includes all the detection fibers binned together and a second CCD channel on CCD camera 110 that includes all the calibration return fibers binned together as depicted in cross-sectional view 123 in FIG. 1.

Fiber optic probe 102 may also include rigid elements 224-228 (e.g., t-tubes and ferrules) that provide stability and/or interfacing capability for fiber optic probe 102. Rigid probe tip 223 may include a plurality of fibers arranged in a configuration as shown in cross-section 120 (see FIG. 1), which comprises an illumination source fiber 122 and eight detection fibers 126. In one embodiment, rigid probe tip 223 is 9.3 cm long and has a diameter of 2.1 mm and can fit within the lumen of a 14 gauge biopsy needle cannula. Although only one source fiber and eight detection fibers are displayed in FIG. 1, any probe tip geometry employing any number of source fibers and detection fibers may be used without departing from the scope of the present subject matter. For example, the illumination core may include a plurality of smaller illumination fibers (i.e., instead of a single illumination source fiber 122) to obtain an illumination core diameter that maximizes the coupling efficiency for the light source, and the signal-to-noise ratio (SNR) for fluorescence measurements (if applicable). In one embodiment, illumination source fiber 122 is used to emit light on a tissue specimen (e.g., sample 118) to be examined. The light may be generated by light source 104 and provided directly to illumination fiber leg 114 of fiber optic probe 102 or via a monochromator (not shown). Specifically, light is emitted into the ends of illumination source fiber 122 and calibration source fiber 124 (i.e., into the common open-ended terminus of ferrule 225). Notably, the light carried by illumination source fiber 122 and calibration source fiber 124 is characterized by the same spectral data.

After the light is emitted by the illumination source fiber 122 on sample 118, at least one detection fiber 126 captures the reflected light (i.e., spectral data of sample) which may ultimately be provided to spectrograph 108 via the fiber array shown in cross-sectional view 123 (see FIG. 1), which is associated with the open-ended terminus of ferrule 228 (see FIG. 2). Notably, the end of detection fiber 126 in fiber array depicted in cross-sectional view 123 corresponds to a terminus of a detection fiber 126 in probe tip cross-sectional view 120 (i.e., each individual detection fiber runs the entire length of collection fiber arm 116 and main portion 222 of probe 102).

Figure 3:
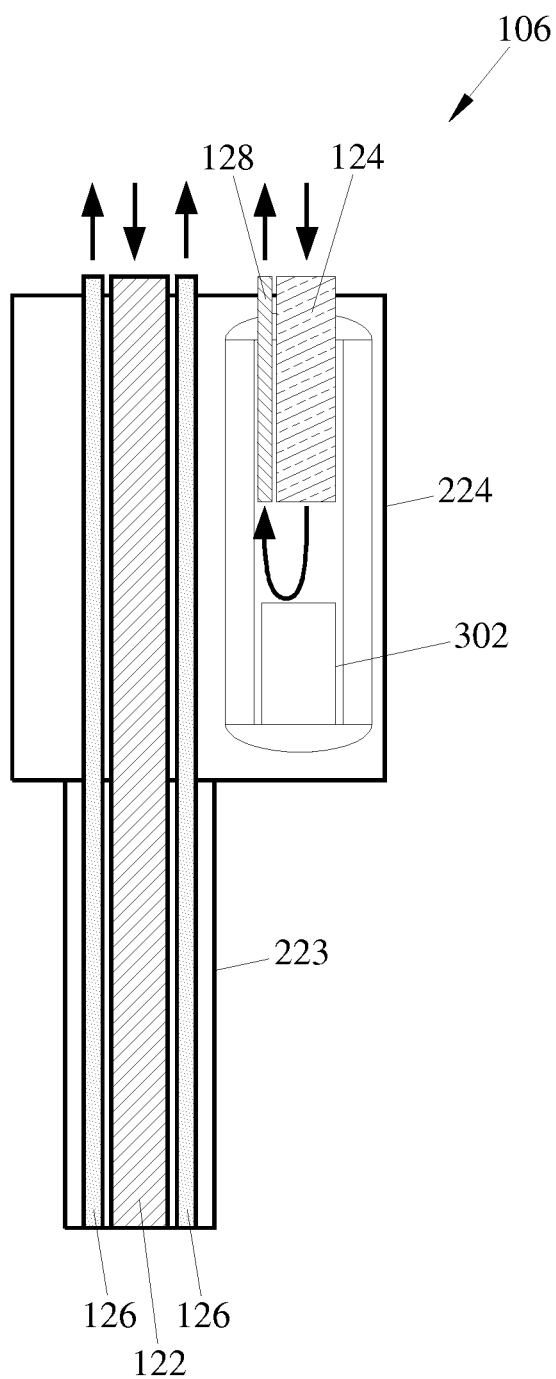
FIG. 3 is a diagram of an exemplary probe tip of a self-calibrating fiber optic probe according to an embodiment of the subject matter described herein.

FIG. 3 is an exemplary self-calibrating fiber optic probe tip section that includes the housing for the self-calibration optical fibers. In one embodiment, probe tip portion 106 receives both illumination source fiber 122 and calibration source fiber 124 from illumination fiber leg 114. As shown in FIG. 3, illumination source fiber 122 passes completely through housing section 224 in order to interface with sample 118. Calibration source fiber 124, however, terminates within housing section 224. In one embodiment, light exits calibration source fiber 124 and is directed to a reflective element 302. Reflective element 302 may include a mirror, a polished metal element (e.g., a polished metal wire), a reflective rod, and the like. After reaching reflective element 302, the light is reflected towards calibration return fiber 128. The reflected light is then received and carried by calibration return fiber 128 to spectrograph 108.

In one embodiment, calibration source fiber 124 and calibration return fiber 128 may comprise the same exact fiber (i.e., a source/return calibration fiber). For example, a single source-return calibration fiber may originate from light source 104, enter housing section 224, and bent or looped back in such a manner that the calibration source/return fiber exits housing section 224. That is, the calibration source-return fiber is bent within housing section 224 in the fiber optic probe such that the calibration source fiber functions as the calibration return fiber (since a mirror or other reflective element is not used). The calibration fiber would then be configured to interface with spectrograph 108 via collection arm 116. Notably, reflective element 302 would not be utilized in this particular embodiment.

Figure 4:
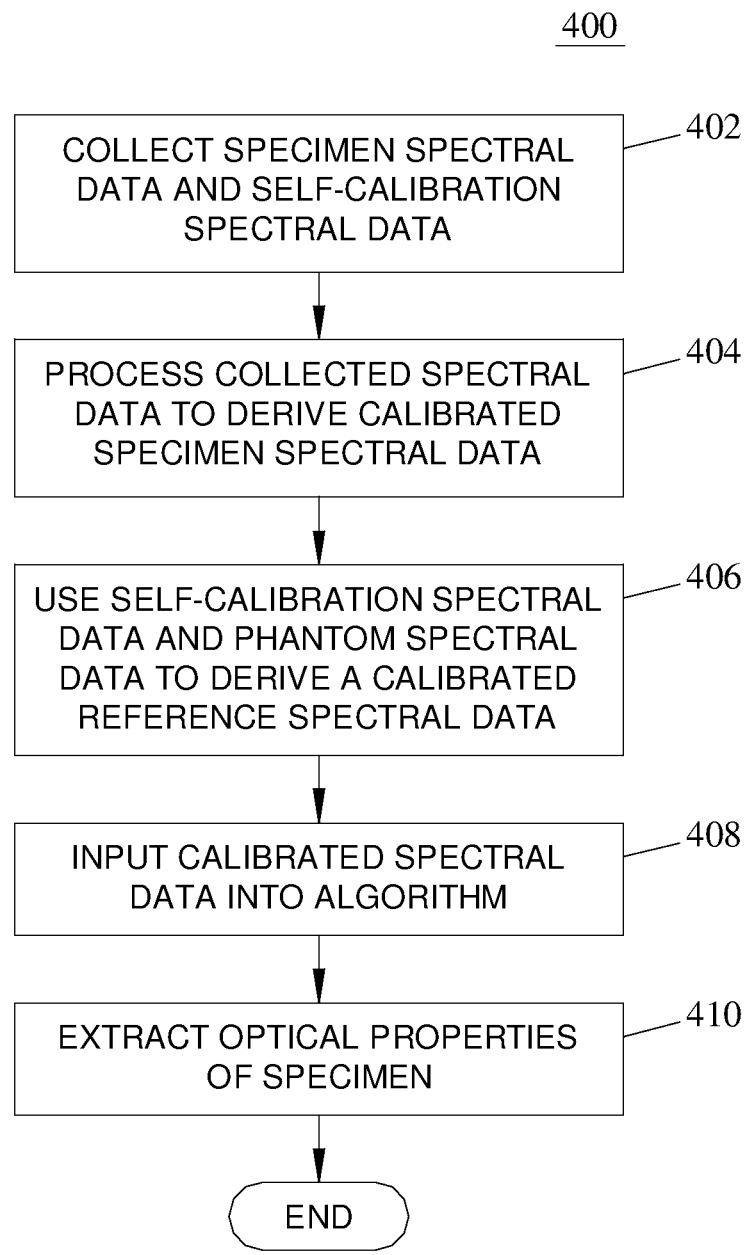
FIG. 4 is a flow chart of an exemplary process for performing optical spectroscopy utilizing a self-calibrating fiber optic probe according to an embodiment of the subject matter described herein.

FIG. 4 depicts an exemplary method 400 for utilizing a self-calibrating fiber optic probe according to an embodiment of the subject matter described herein. In block 402, specimen spectral data and self-calibration spectral data are collected. In one embodiment, illumination light originating from light source 104 and carried by illumination source fiber 122 is emitted on sample 118. The illumination light is diffusely reflected off of sample 118 at one or more wavelengths and may be collected by one or more detection fibers 126, which in turn carry the reflected light to spectrograph 108.

At the same time the illumination light from light source 104 traverses illumination source fiber 122, light (i.e., calibration light) is traversing calibration source fiber 124. More specifically, the calibration light and the illumination light are generated by light source 104 at the same time and contemporaneously traverse illumination fiber leg 114. While the light traversing illumination source fiber 122 proceeds to sample 118, the light in calibration source fiber 124 is directed to reflection element 302. The reflected light from calibration source fiber 124 is then directed to and received by calibration return fiber 128, which in turn carries the reflected light to spectrograph 108. In one embodiment, spectrograph 108 receives the reflected light in calibration return fiber 128 contemporaneously with the diffusely reflected light carried by detection fibers 126.

In block 404, the collected spectral data is processed to derive calibrated specimen spectral data. In one embodiment, the specimen spectral data (i.e., diffusely reflected light) is divided by the calibration spectral data (i.e., reflected light from calibration return fiber 128) on a spectrum point by point basis to obtain calibrated specimen spectral data. This calibration of the specimen spectral data is performed to account for real-time intensity fluctuations of the light source and fiber bending effects, as well as wavelength dependent system response in system 100.

In one embodiment, the calibration spectral data may have a correlation factor applied before being processed with the specimen spectral data. Because the calibration channel may have wavelength responses that differ from the wavelength responses exhibited in the sensing channel, the wavelength response in the calibration channel may require correction and/or compensation. For example, to correct the calibration channel's wavelength dependence, a spectral measurement may be taken from a reflectance standard (e.g., a Spectralon puck), which is characterized by a flat wavelength response. A correction factor may be generated for each probe by dividing the spectral data of the reflectance standard by the self-calibration spectrum (e.g., the spectral data of the light provided to spectrograph 108 by calibration return fiber 128) concurrently obtained with the spectral data of the reflectance standard. For example, the correlation factor may be the ratio, $F_{corr}(\lambda)=[R_{Puck}(\lambda)]/[R_{SC}(\lambda)]$, which serves as correction of the calibration channel in terms of wavelength response. Notably, this correlation factor need only be determined once and can be used for the lifetime of a given self-calibrating fiber optic probe.

In block 406, the self-calibration spectral data and reference spectral data are used to derive calibrated reference spectral data. In one embodiment, reference spectral data includes spectral data of a phantom (i.e., a model that simulates human tissue and blood vessels). The reference spectral data is also divided by the aforementioned self-calibration spectral data (with or without the application of the correlation factor) on a spectrum point by point basis to obtain calibrated reference spectral data. Although method 400 depicts block 406 being performed after block 404, the collection of the reference spectral data is a one time procedure for each probe and instrument combination and may instead be performed before block 404 without departing from the scope of the present subject matter.

In block 408, the calibrated spectral data is input into an algorithm. In one embodiment, both the calibrated tissue spectral data and the calibrated reference spectral data respectively obtained in block 404 and 406 are input into an inverse Monte Carlo model algorithm executed by processing unit 112.

In block 410, optical properties of the specimen are extracted. In one embodiment, once the calibrated spectral data is processed via the inverse Monte Carlo model, the processing unit 112 is configured to derive optical properties (e.g., scatterers and absorbers) of sample 118.

It will be understood that various details of the presently disclosed subject matter may be changed without departing from the scope of the presently disclosed subject matter. Furthermore, the foregoing description is for the purpose of illustration only, and not for the purpose of limitation.

What is claimed is:

1. A self-calibrating fiber optic probe comprising:
   a sensing channel for transmitting illumination light to a specimen and for collecting spectral data of the specimen, wherein the spectral data includes the illumination light diffusely reflected from the specimen at one or more wavelengths, wherein the sensing channel includes at least one illumination source fiber for transmitting the illumination light to the specimen and at least one detection fiber for collecting the illumination light diffusely reflected from the specimen; and
   a calibration channel for transmitting calibration light, wherein the calibration light and the illumination light are generated simultaneously from a common light source, and collecting calibration spectral data associated with the calibration light contemporaneously with the collection of the spectral data of the specimen, wherein the calibration channel includes at least one calibration source fiber for transmitting the calibration light and at least one calibration return fiber for receiving at least a portion of the calibration light from the at least one calibration source fiber and wherein the at least one calibration source fiber and the at least one illumination source fiber comprise separate fibers having identical numerical apertures.

2. The fiber optic probe of claim 1 wherein the at least one calibration source fiber and the at least one calibration return fiber are the same optical fiber.

3. The fiber optic probe of claim 2 wherein the at least one calibration source fiber is bent within a probe tip housing section in the fiber optic probe such that the at least one calibration source fiber functions as the at least one calibration return fiber.

4. The fiber optic probe of claim 1 wherein the at least one calibration source fiber and the at least one illumination source fiber are constructed from the same type of materials and include identical core diameters and clad diameters, and wherein the at least one detection fiber and the at least one calibration return fiber are constructed from the same type of materials and include identical numerical apertures, core diameters and clad diameters.

5. The fiber optic probe of claim 1 wherein the at least one calibration source fiber directs at least a portion of the calibration light to a reflective element to be reflected to and received by the at least one calibration return fiber.

6. The fiber optic probe of claim 5 wherein the reflective element includes at least one of a mirror, a reflective rod, and a polished metal element.

7. The fiber optic probe of claim 1 wherein the at least one calibration return fiber and the at least one detection fiber are coupled to at least one of a spectrograph, spectrometer, or photodetector.

8. The fiber optic probe of claim 1 wherein the at least one calibration return fiber is coupled to at least one of a first spectrograph, a first spectrometer, or a first photodetector, and the at least one detection fiber is coupled to at least one of a second spectrograph, a second spectrometer, or a second photodetector.

9. The fiber optic probe of claim 1 wherein the at least one calibration return fiber includes a primary calibration return fiber and a backup calibration return fiber.

10. The fiber optic probe of claim 1 wherein the specimen includes a tissue or a turbid medium.

11. The fiber optic probe of claim 1 wherein the fiber optic probe comprises at least one of a forward firing fiber optic probe or a side firing fiber optic probe.

12. The fiber optic probe of claim 1 wherein the calibration channel includes a reflective element, wherein the at least one calibration source fiber directs at least a portion of the calibration light to the reflective element to be reflected to and received by the at least one calibration return fiber, wherein the calibration channel further includes a housing for housing the at least one calibration source fiber, the at least one calibration return fiber, and the reflective element, wherein the at least one calibration source fiber terminates within the housing, and wherein the at least one illumination source fiber extends completely through the housing to interface with the specimen.

13. A system for performing self-calibrating diffuse reflectance spectroscopy, the system comprising:
a fiber optic probe that includes: a sensing channel for transmitting illumination light to a specimen and for collecting spectral data of the specimen, wherein the spectral data includes the illumination light diffusely reflected at one or more wavelengths from the specimen, wherein the sensing channel includes at least one illumination source fiber for transmitting the illumination light to the specimen and at least one detection fiber for collecting the illumination light diffusely reflected from the specimen; and
a calibration channel for transmitting calibration light, wherein the calibration light and the illumination light are generated simultaneously from a light source, and for collecting calibration spectral data associated with the calibration light contemporaneously with the collection of the spectral data of the specimen, wherein the calibration channel includes at least one calibration source fiber for transmitting the calibration light and at least one calibration return fiber for receiving at least a portion of the calibration light from the at least one calibration source fiber and wherein the at least one calibration source fiber and the at least one illumination source fiber comprise separate fibers having identical numerical apertures;
a processing unit, coupled to the sensing channel and the calibration channel, for receiving the spectral data of the specimen and the calibration spectral data to generate calibrated specimen spectral data in real-time.

14. The system of claim 13 wherein the at least one calibration source fiber and the at least one calibration return fiber are the same optical fiber.

15. The system of claim 13 wherein the at least one calibration source fiber is bent within a probe tip housing section in the fiber optic probe such that the at least one calibration source fiber functions as the at least one calibration return fiber.

16. The system of claim 13 wherein the at least one calibration source fiber and the at least one illumination source fiber are constructed from the same type of materials and include identical, core diameters and clad diameters, and wherein the at least one detection fiber and the at least one calibration return fiber are constructed from the same type of materials and include identical numerical apertures, core diameters and clad diameters.

17. The system of claim 13 wherein the at least one calibration source fiber directs at least a portion of the calibration light to a reflective element to be reflected to and received by the at least one calibration return fiber.

18. The system of claim 17 wherein the reflective element includes at least one of a mirror, a reflective rod, and a polished metal element.

19. The system of claim 13 wherein the at least one calibration return fiber includes a primary calibration return fiber and a backup calibration return fiber.

20. The system of claim 13 wherein the specimen includes a tissue or a turbid medium.

21. The system of claim 13 wherein the fiber optic probe comprises at least one of a forward firing fiber optic probe or a side firing fiber optic probe.

22. The system of claim 13 wherein the light source includes at least one of a xenon lamp or a white light emitting diode (LED) source.

23. The system of claim 13, wherein the processing unit comprises a spectrometer and a computer for receiving contemporaneously the spectral data of the specimen from the at least one detection fiber and the calibration spectral data from the at least one calibration return fiber.

24. The system of claim 23 wherein the calibration spectral data represents effects of at least one of real-time light source intensity fluctuations and real-time attenuation of the calibration light caused by bending of the fiber optic probe.

25. The system of claim 24 wherein the processing unit applies a correlation factor to the calibration spectral data to generate modified calibration spectral data.

26. The system of claim 25 wherein the correlation factor comprises a ratio between spectral data associated with a diffuse reflectance standard and the calibration spectral data that is collected concurrently.

27. The system of claim 26 wherein the processing unit processes the spectral data of the specimen and the modified calibration spectral data to produce calibrated specimen spectral data.

28. The system of claim 27 wherein the calibrated specimen spectral data is an input to a Monte Carlo algorithm or a diffusion algorithm that derives optical properties of the specimen.

29. The system of claim 28 wherein the Monte Carlo algorithm includes either an inverse Monte Carlo reflectance algorithm or an inverse Monte Carlo fluorescence algorithm.

30. The system of claim 29 wherein the diffusion algorithm includes an inverse diffusion algorithm.

31. The system of claim 13 wherein the calibration channel includes a reflective element, wherein the at least one calibration source fiber directs at least a portion of the calibration light to the reflective element to be reflected to and received by the at least one calibration return fiber, wherein the calibration channel further includes a housing for housing the at least one calibration source fiber, the at least one calibration return fiber, and the reflective element, wherein the at least one calibration source fiber terminates within the housing, and wherein the at least one illumination source fiber extends completely through the housing to interface with the specimen.

32. A method for utilizing a self-calibrating fiber optic probe comprising:
transmitting illumination light via a sensing channel from a light source to a specimen, wherein the sensing channel includes at least one illumination source fiber for transmitting the illumination light to the specimen and at least one detection fiber for collecting the illumination light diffusely reflected from the specimen;

transmitting calibration light via a calibration channel, wherein the calibration light and the illumination light are generated simultaneously from the light source, wherein the calibration channel includes at least one calibration source fiber for transmitting the calibration light and at least one calibration return fiber for receiving at least a portion of the calibration light from the at least one calibration source fiber and wherein the at least one calibration source fiber and the at least one illumination source fiber comprise separate fibers having identical numerical apertures;

collecting spectral data of the specimen via the sensing channel, wherein the spectral data includes the illumination light diffusely reflected from the specimen at one or more wavelengths; and collecting calibration spectral data associated with the calibration light via the calibration channel contemporaneously with the collection of the spectral data of the specimen.

33. The method of claim 32 wherein the at least one calibration source fiber and the at least one calibration return fiber are the same optical fiber.

34. The method of claim 33 wherein the at least one calibration source fiber is bent within a probe tip housing section in the method such that the at least one calibration source fiber functions as the at least one calibration return fiber.

35. The method of claim 32 wherein the at least one calibration source fiber and the at least one illumination source fiber are constructed from the same type of materials and include identical, core diameters and clad diameters, and wherein the at least one detection fiber and the at least one calibration return fiber are constructed from the same type of materials and include identical numerical apertures, core diameters and clad diameters.

36. The method of claim 32 further comprising:
directing at least a portion of the calibration light via the at least one calibration source fiber to a reflective element to be reflected to and received by the at least one calibration return fiber.

37. The method of claim 36 wherein the reflective element includes at least one of a mirror, a reflective rod, and a polished metal element.

38. The method of claim 32 wherein the at least one calibration return fiber and the at least one detection fiber are coupled to at least one of a spectrograph, spectrometer, or photodiode.

39. The method of claim 32 wherein the at least one calibration return fiber is coupled to at least one of a first spectrograph, a first spectrometer, or a first photodiode, and the at least one detector fiber is coupled to at least one of a second spectrograph, a second spectrometer, or a second photodiode.

40. The method of claim 32 wherein the at least one calibration return fiber includes a primary calibration return fiber and a backup calibration return fiber.

41. The method of claim 32 wherein the specimen includes a tissue or a turbid medium.

42. The method of claim 32 wherein the method comprises at least one of a forward firing fiber optic probe or a side firing fiber optic probe.

43. The method of claim 32 wherein the calibration channel includes a reflective element, wherein the at least one calibration source fiber directs at least a portion of the calibration light to the reflective element to be reflected to and received by the at least one calibration return fiber, wherein the calibration channel further includes a housing for housing the at least one calibration source fiber, the at least one calibration return fiber, and the reflective element, wherein the at least one calibration source fiber terminates within the housing, and wherein the at least one illumination source fiber extends completely through the housing to interface with the specimen.

* * * * *